(12) United States Patent
Leyes

(10) Patent No.: US 8,258,161 B2
(45) Date of Patent: Sep. 4, 2012

(54) CRYSTALLINE SALT FORM OF AN ANTIDIABETIC COMPOUND

(75) Inventor: Aquiles E. Leyes, Schwenksville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 361 days.

(21) Appl. No.: 12/529,202

(22) PCT Filed: Feb. 28, 2008

(86) PCT No.: PCT/US2008/055282
§ 371 (c)(1),
(2), (4) Date: Aug. 31, 2009

(87) PCT Pub. No.: WO2008/109334
PCT Pub. Date: Sep. 12, 2008

(65) Prior Publication Data
US 2010/0056580 A1     Mar. 4, 2010

Related U.S. Application Data

(60) Provisional application No. 60/904,510, filed on Mar. 2, 2007.

(51) Int. Cl.
*A61K 31/4439* (2006.01)
*C07D 413/04* (2006.01)
(52) U.S. Cl. .................................... 514/338; 546/272.1
(58) Field of Classification Search ............... 546/272.1; 514/338
See application file for complete search history.

(56) References Cited

U.S. PATENT DOCUMENTS 6,627,646 B2 * 9/2003 Bakale et al. ................. 514/322
2009/0264473 A1 * 10/2009 Song et al. .................... 514/338

FOREIGN PATENT DOCUMENTS

WO    2006/096564 A1   9/2006
WO    2006/099077 A1   9/2006

OTHER PUBLICATIONS

Chemical & Engineering News, Feb. 2003, 32-35.*
Brittain ed., "Polymorphism in Pharmaceutical Science.," NY:Marcel Dekker, Inc., 1999, 1-2, 183-226, 235-238.*
U.S. Pharmacopia #23, National Formulary #18, 1995, 1843-1844.*
Muzaffar et al., "Polymorphism and Drug Availability, etc.," J of Pharm. (Lahore), 1979, 1(1), 59-66.*
Jain et al., "Polymorphism in Pharmacy", Indian Drugs, 1986, 23(6) 315-329.*
Taday et al., "Using Terahertz, etc.," J of Pharm. Sci., 92(4), 2003, 831-838.*
Concise Encyclopedia Chemistry, NY: Walter de Gruyter, 1993, 872-873.*
Rowland & Tozer, "Clinical Pharmacokinetics, etc.," 1995, p. 123.*
Silverman, The Organic Chemistry of Drug Design and Drug Action, NY: Academic Press, 1993, 72-76.*
Ulicky. Comprehensive Dictionary of Physical Chemistry, NY: Prentice Hall, 1992, p. 21.*
Doelker, english translation of Ann. Pharm. Fr., 2002, 60: 161-176, pp. 1-39.*
Doelker, english translation of S.T.P, Pratiques (1999), 9(5), 399-409, pp. 1033.*
Otuska et al., "Effect of Polymorphic, etc.," Chem. Pharm. Bull., 47(6) 852-856 (1999).*
CMU Pharmaceutical polymorphism, internet, p. 1-3 (2002) (print out Apr. 3, 2008).*
Singhal et al., "Drug Polymorphism, etc.," Advanced Drug Delivery reviews 56, p. 335-347 (2004).*

* cited by examiner

*Primary Examiner* — Patricia Morris
(74) *Attorney, Agent, or Firm* — Anna L. Cocuzzo; Richard C. Billups

(57) ABSTRACT

A novel crystalline anhydrous toluenesulfonic acid salt form of a selective PPAR gamma partial agonist which has a fused bicyclic aromatic group attached to an oxypropanoic acid moiety is stable and non-hygroscopic. The crystalline salt form is useful for making pharmaceutical formulations for the treatment of type 2 diabetes, hyperglycemia, obesity, and dyslipidemia.

11 Claims, 3 Drawing Sheets

CRYSTALLINE SALT FORM OF AN ANTIDIABETIC COMPOUND

CROSS-REFERENCE TO RELATED APPLICATIONS

This application is a U.S. National Phase application under 35 U.S.C. §371 of PCT Application No. PCT/US2008/055282, filed Feb. 28, 2008, which published as WO 2008/109334 on Sept. 12, 2008, and claims priority under 35 U.S.C. §119 from U.S. Provisional Application No. 60/904,510, filed Mar. 2, 2007.

FIELD OF THE INVENTION

The present invention relates to a novel crystalline salt form of a compound that is useful as a pharmaceutically active ingredient for the treatment of type 2 diabetes and other diseases that are modulated by PPAR gamma agonists, including hyperglycemia, obesity, dyslipidemia, and the metabolic condition.

BACKGROUND OF THE INVENTION

Type 2 diabetes remains a serious medical problem. There is an ongoing need for new treatments that are more effective and that have fewer side effects. PPAR gamma agonists, including the two marketed products rosiglitazone and pioglitazone, are important medications for the treatment of type 2 diabetes. Treatment of a patient with PPAR gamma agonists improves insulin sensitivity, but the treatment is often accompanied by side effects, such as weight gain and edema. Selective PPAR gamma partial agonists, also known as selective PPAR gamma modulators (SPPARM's or SPPARgM's), are effective in reducing serum glucose with reduced weight gain and/or edema.

SUMMARY OF THE INVENTION

The present invention is concerned with a novel crystalline salt form of a compound that is an active PPAR gamma partial agonist, and methods of making the novel crystalline salt. The compound was originally disclosed in PCT application WO2006/096564. The crystalline salt form disclosed herein is novel and well characterized, and has advantages over the solid compound disclosed in WO2006/096564 that makes it useful in preparing pharmaceutical formulations, such as ease of purification, ease of processing, and thermodynamic stability with respect to other forms of the compound.

The invention also concerns pharmaceutical compositions comprising the novel crystalline salt form; methods for the preparation of the salt form and pharmaceutical compositions; and methods for using the salt form and formulations for the treatment of type 2 diabetes, hyperglycemia, obesity, dyslipidemia, and the metabolic condition.

DETAILED DESCRIPTION OF THE INVENTION

Figure 1:
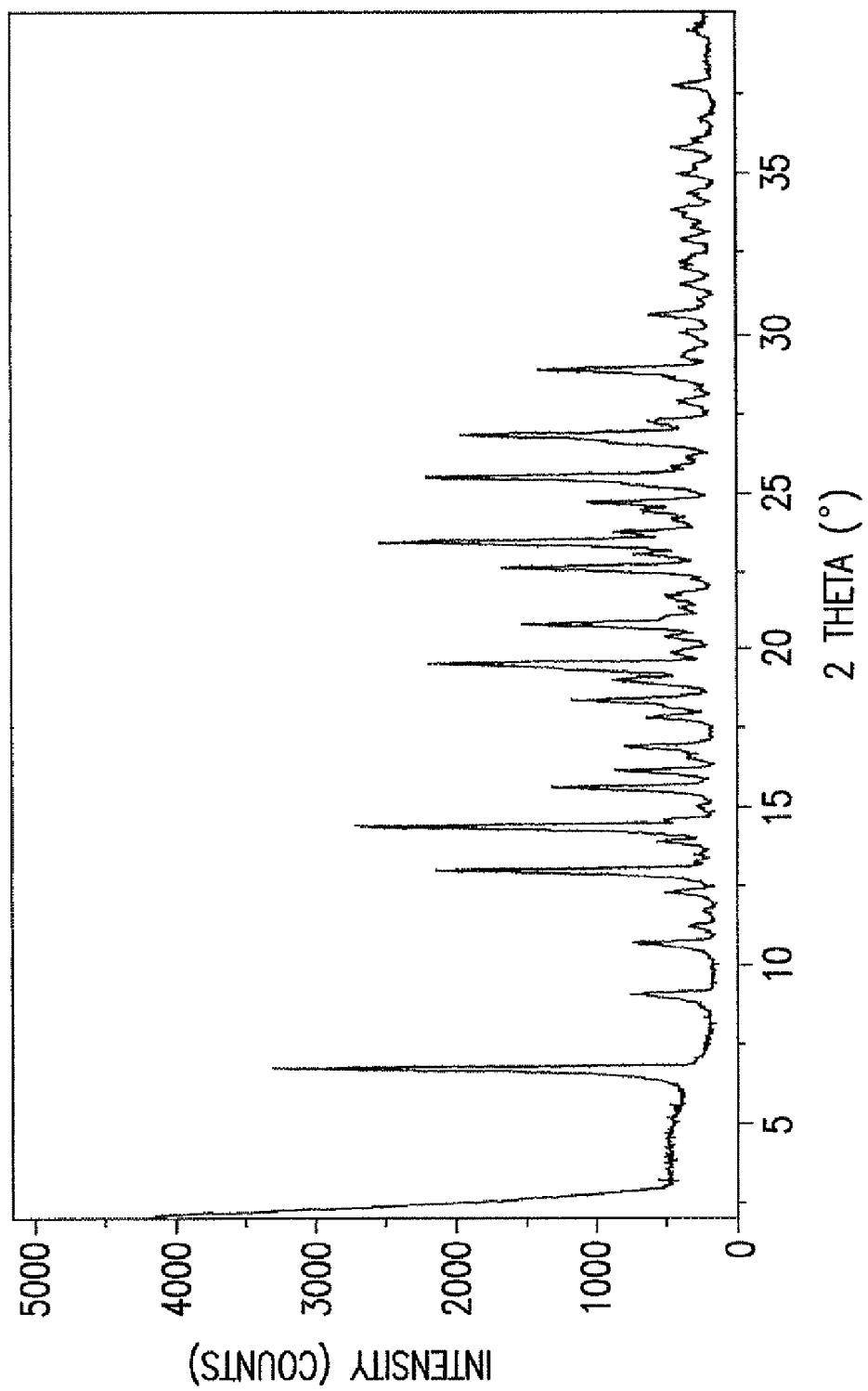
FIG. 1 is a characteristic X-ray diffraction pattern of the crystalline anhydrous tosylate salt.

In one embodiment, this application provides a novel toluenesulfonic acid salt (tosylate) of (2S)-2-({6-chloro-3-[6-(4-chlorophenoxy)-2-propylpyridin-3-yl]-1,2-benzisoxazol-5-yl}oxy)propanoic acid (Compound I):

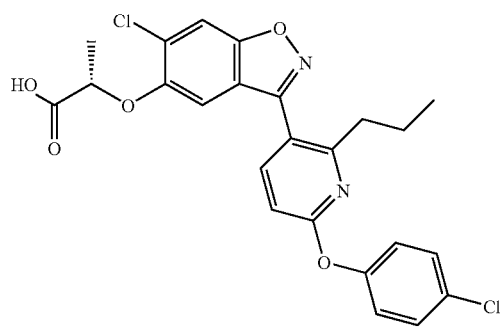

In a second embodiment, this application provides an anhydrous crystalline tosylate salt of (2S)-2-({6-chloro-3-[6-(4-chlorophenoxy)-2-propylpyridin-3-yl]-1,2-benzisoxazol-5-yl}oxy)propanoic acid (Compound I) that is particularly advantageous for preparing pharmaceutical compositions and formulations.

The toluenesulfonic acid (tosylate) salt of Compound I is also a new composition of matter (a new chemical compound). This is generally referred to herein as the toluenesulfonic acid (tosylate) salt of Compound I, but it can also be written as a chemical compound having Formula Ia:

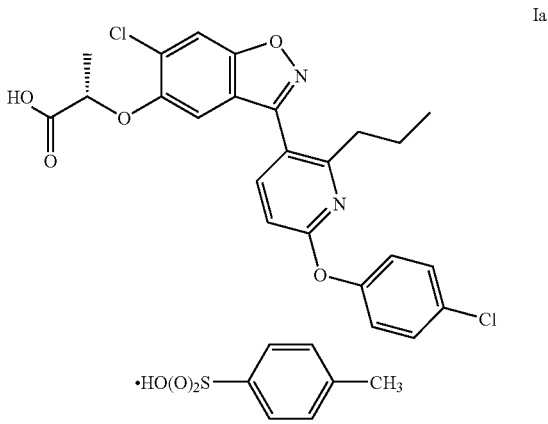

The compositions, drug substances, formulations, and pharmaceutical uses that are described herein for the specific crystalline anhydrous tosylate salt are also representative of compositions, drug substances, formulations, and pharmaceutical uses of the tosylate salt in general.

A further embodiment of the present invention provides a drug substance that comprises the crystalline anhydrous toluenesulfonic acid salt of Compound I in a detectable amount. By "drug substance" is meant the active pharmaceutical ingredient (API). The amount of crystalline anhydrous toluenesulfonic acid salt of Compound I in the drug substance can be quantified by the use of physical methods such as X-ray powder diffraction (XRPD), solid-state fluorine-19 magic-angle spinning (MAS) nuclear magnetic resonance spectroscopy, solid-state carbon-13 cross-polarization magic-angle spinning (CPMAS) nuclear magnetic resonance spectroscopy, solid state Fourier-transform infrared spectroscopy, and Raman spectroscopy. In a sub-class of this embodiment, about 5% to about 100% by weight of the crystalline anhydrous toluenesulfonic acid salt of Compound I is present in the drug substance. In a second sub-class of this embodiment, about 10% to about 100% by weight of the crystalline anhydrous toluenesulfonic acid salt of Compound I is present in the drug substance. In a third sub-class of this embodiment, about 25% to about 100% by weight of the crystalline anhydrous toluenesulfonic acid salt of Compound I is present in the drug substance. In a fourth sub-class of this embodiment, about 50% to about 100% by weight of the crystalline anhydrous toluenesulfonic acid salt of Compound I is present in the drug substance. In a fifth sub-class of this embodiment, about 75% to about 100% by weight of the crystalline anhydrous toluenesulfonic acid salt of Compound I is present in the drug substance. In a sixth sub-class of this embodiment, substantially all of the Compound I drug substance is the crystalline anhydrous toluenesulfonic acid salt of Compound I, i.e., the Compound I drug substance is the substantially phase pure crystalline anhydrous toluenesulfonic acid salt of Compound I.

Another aspect of the present invention provides a method for the treatment or control of clinical conditions for which a PPAR gamma agonist is indicated, which method comprises administering to a patient in need of such treatment or control a therapeutically effective amount of the crystalline anhydrous toluenesulfonic acid salt of Compound I or a pharmaceutical composition containing a therapeutically effective amount of the crystalline anhydrous toluenesulfonic acid salt of Compound I. Such clinical conditions include Type 2 diabetes, hyperglycemia, obesity, dyslipidemia, and metabolic syndrome. A "patient" is a mammal, including a human. A patient is most often a human patient.

The present invention also provides for the use of the crystalline anhydrous toluenesulfonic acid salt of Compound I of the present invention in the manufacture of a medicament for the treatment or control in a patient of one or more clinical conditions for which a PPAR gamma agonist is indicated. In one embodiment, the clinical condition is Type 2 diabetes.

Another aspect of the present invention provides the crystalline anhydrous toluenesulfonic acid salt of Compound I for use in the treatment or control in a patient of one or more clinical conditions for which a PPAR gamma agonist is indicated. In one embodiment of this aspect the clinical condition is Type 2 diabetes.

The present invention also provides pharmaceutical compositions comprising the crystalline anhydrous toluenesulfonic acid salt of Compound I in association with one or more pharmaceutically acceptable carriers or excipients. In one embodiment the pharmaceutical composition comprises the active pharmaceutical ingredient (API) in admixture with pharmaceutically acceptable excipients wherein the API comprises a detectable amount of the crystalline anhydrous toluenesulfonic acid salt of Compound I. In a sub-class of this embodiment the pharmaceutical composition comprises the API in admixture with pharmaceutically acceptable excipients wherein the API comprises about 5% to about 100% by weight of the crystalline anhydrous toluenesulfonic acid salt of Compound I. In a sub-class of this second embodiment, the API in such compositions comprises about 10% to about 100% by weight of the crystalline anhydrous toluenesulfonic acid salt of Compound I. In a subclass of this embodiment, the API in such compositions comprises about 25% to about 100% by weight of the crystalline anhydrous toluenesulfonic acid salt of Compound I. In a sub-class of this embodiment, the API in such compositions comprises about 50% to about 100% by weight of the crystalline anhydrous toluenesulfonic acid salt of Compound I. In a sub-class of this embodiment, the API in such compositions comprises about 75% to about 100% by weight of the crystalline anhydrous toluenesulfonic acid salt of Compound I. In a sub-class of this embodiment, substantially all of the API is crystalline anhydrous toluenesulfonic acid salt of Compound I, i.e., the API is substantially phase pure Compound I in the form of a crystalline anhydrous toluenesulfonic acid salt of Compound I.

The compositions in accordance with the invention are suitably in unit dosage forms such as tablets, pills, capsules, powders, granules, sterile solutions or suspensions, metered aerosol or liquid sprays, drops, ampoules, auto-injector devices or suppositories. The compositions are intended for oral, parenteral, intranasal, sublingual, or rectal administration, or for administration by inhalation or insufflation. Formulation of the compositions according to the invention can conveniently be effected by methods known from the art, for example, as described in *Remington's Pharmaceutical Sciences* 17$^{th}$ ed., 1995.

The dosage regimen is selected in accordance with a variety of factors including type, species, age, weight, sex and medical condition of the patient; the severity of the condition to be treated; the route of administration; and the renal and hepatic function of the patient. An ordinarily skilled physician, veterinarian, or clinician can readily determine and prescribe the effective amount of the drug required to prevent, counter or arrest the progress of the condition or to treat or control the condition.

Oral administration is the preferred method of administering the crystal forms and salt forms of Compound I described herein. The drug can be administered 1-2 times per day, with once daily being preferred. The daily dosage for an adult human patient is generally 1-25 mg (free acid equivalent), and preferably 2-10 mg (free acid equivalent) administered once daily.

In the methods of the present invention, the crystalline anhydrous toluenesulfonic acid salt of Compound I described in detail herein can form the API, and is typically administered in admixture with suitable pharmaceutical diluents, excipients or carriers (collectively referred to herein as 'carrier' materials) suitably selected with respect to the intended form of administration, that is, oral tablets, capsules, elixirs, syrups and the like, and consistent with conventional pharmaceutical practices.

For instance, for oral administration in the form of a tablet or capsule, the active pharmaceutical ingredient can be combined with an oral, non-toxic, pharmaceutically acceptable, inert carrier such as lactose, starch, sucrose, glucose, methyl cellulose, microcrystalline cellulose, magnesium stearate, calcium sulfate, mannitol, sorbitol and the like; for oral administration in liquid form, the oral API can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, some natural sugars, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, and the like. Disintegrants include, without limitation, starch, methyl cellulose, croscarmellose sodium, agar, bentonite, xanthan gum and the like. Surfactants, such as sodium lauryl sulfate, can also be included in the formulations.

The following non-limiting Examples are intended to illustrate the present invention and should not be construed as being limitations on the scope or spirit of the instant invention.

Example 1

Synthesis of (2S)-2-({6-chloro-3-[6-(4-chlorophenoxy)-2-propylpyridin-3-yl]-1,2-benzisoxazol-5-yl}oxy)propanoic acid (Compound I)

Compound I is made by the multi-step process shown in Schemes 1 and 2 below. The process is described in detail in the description after the examples. Compound I as the free acid is (S)-14 in the schemes and description below.

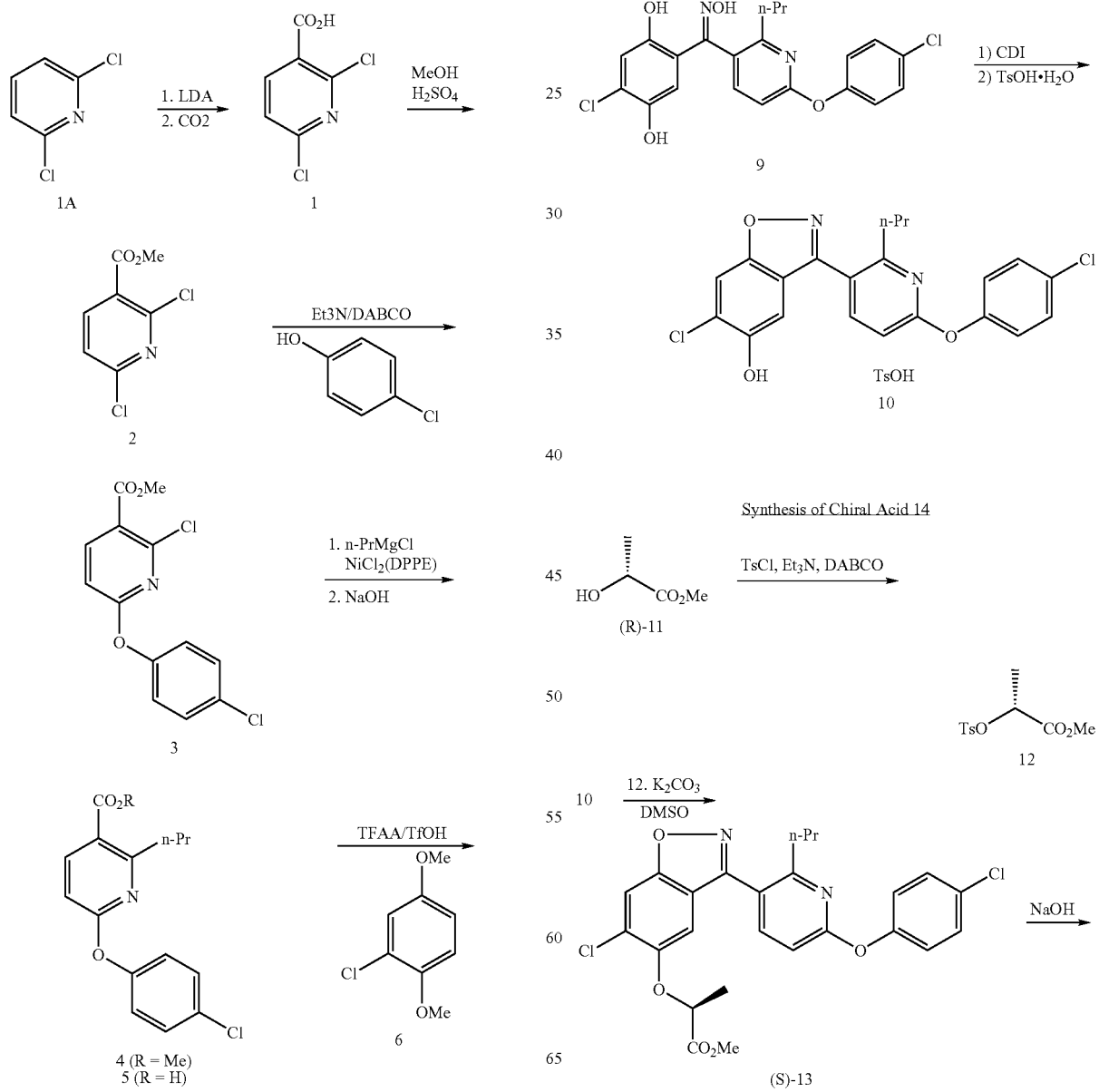

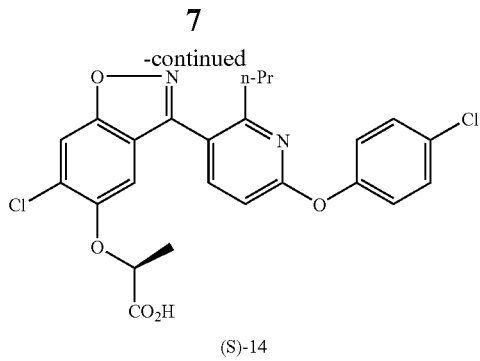

(S)-14

Steps 1 and 2. Esterification and Aryl Ether Formation

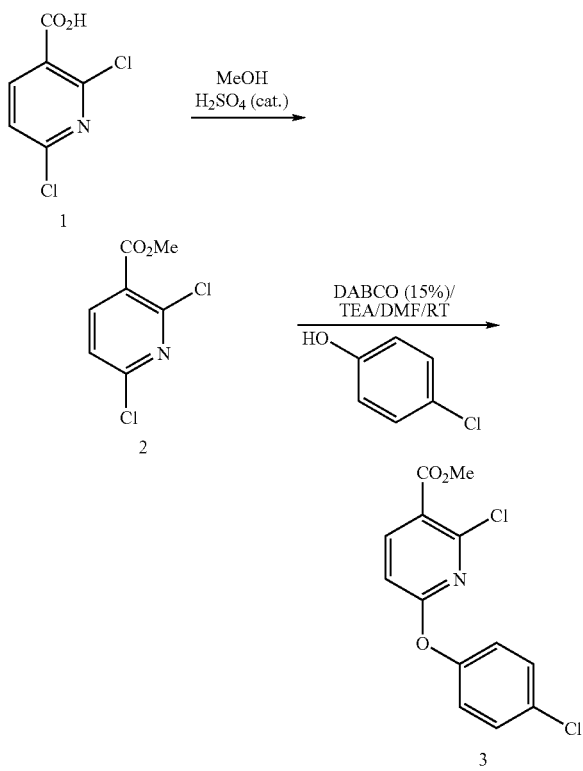

To a solution of 2,6-dichloronicotinic acid (1) (19.2 g, 0.0 mol) in MeOH (100 mL) was added 5.56 mL (0.10 mol) of concentrated $H_2SO_4$ dropwise. An ~15° C. temperature increase was observed. The resulting solution was heated at 60° C. for 8-14 hrs.

The reaction mixture was allowed to cool to RT and then poured into a biphasic mixture containing IPAc (220 mL) and aq. $K_2CO_3$ (20.7 g in 117.3 g water) at RT with stirring. The organic layer was separated, washed with sat. $NaHCO_3$ (80 mL), and then water (80 mL). The isolated IPAc solution was subjected to a solvent switch to DMF (80 mL) in vacuo.

A solution of 4-chlorophenol (12.2 g, 0.095 mol) in 36.6 mL of DMF was added at room temperature to the above solution (19.6 g of ester 2, 0.095 mol), followed by addition of triethylamine (17.3 mL, 0.124 mol) at 20-22° C. over 15 min. Solid DABCO (1.6 g, 14.2 mmol) was added to the resulting solution in one portion. A temperature increase of ~3° C. was observed. A water bath was used to maintain the reaction temperature. The reaction was stirred at 22-24° C. for 4-5 h while monitoring by LC until all of the 4-chlorophenol was consumed, resulting in a light slurry. AcOH (2.72 mL, 47.5 mmol) and IPA (57.5 mL) were added to the light slurry, followed by cold water (30 mL) to maintain the internal temperature at 20-25° C. When the water was added, a clear solution first formed, and then a slurry of product formed. After stirring at RT for 0.5 h, additional water (86 mL) was added over 0.5 h. After the slurry was stirred at RT for 1-2 h, it was filtered. The filter cake was washed with mixed solvents (60 mL of IPA-$H_2O$=1:1). The isolated solid was dried in a vacuum-oven at 50° C. for 8 h to provide the product as white cotton-like solid.

Step 3. Propylation

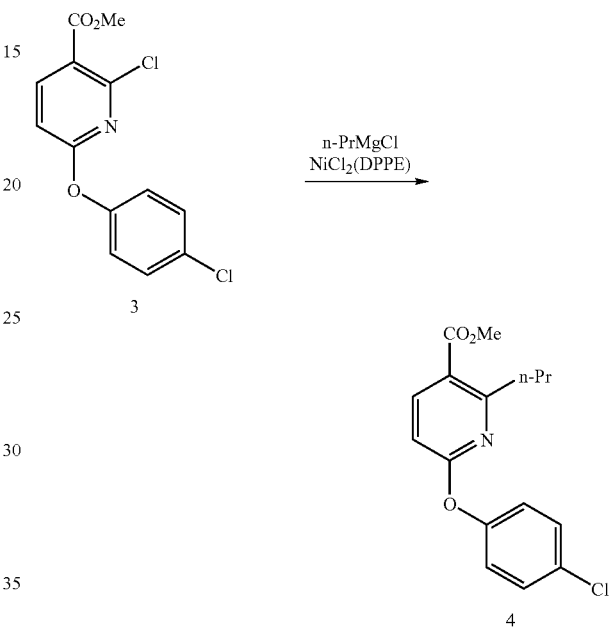

To a solution of methyl 2-chloro-6-(4-chlorophenoxy) nicotinate (12.53 g, 42.03 mmol) and NiCl$_2$dppe (111 mg, 0.5 mol %) in THF (63 mL) was added n-PrMgCl (2.0 M in diethyl ether, 22.5 mL, 45.0 mmol) over ½ h. The reaction was aged at 25° C. to 28° C. for 15 minutes.

The reaction was then quenched with 10% citric acid solution (120 mL) and diluted with MTBE (120 mL). The mixture was stirred over 15 min. The organic layer was cut and was washed with 10% NaCl solution (120 mL). The organic layer (188 mL) was concentrated to 90 mL (½ volume), and 90 mL of MeOH was then added. The volume was again reduced to 90 mL by vacuum distillation. This was repeated 2 additional times to complete the solvent switch to MeOH. The final volume was about 90 mL.

Step 4. Methyl Ester Hydrolysis

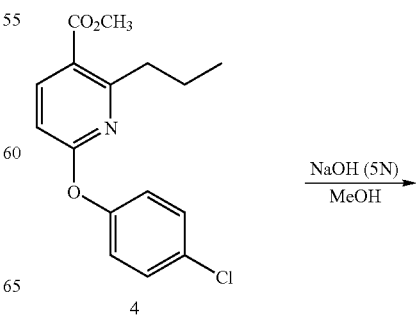

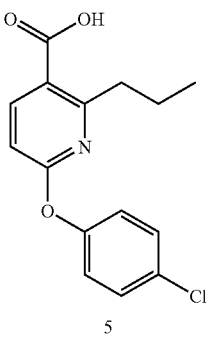

To the solution of 4 from above was added 5N NaOH (13 mL, 65 mmol). The mixture was heated to 68° C. for 2.5 h. LC assay showed the reaction was complete. The reaction can also be run at 50° C., in which case it is typically complete in 4 h. Water (90 mL) was then added to the solution at 68° C., followed by 36 mL of 20% citric acid. The product crystallized from the solution. Water (90 mL) was then added. The slurry was stirred for 2 h and was then filtered. The white cake was washed with 150 mL of water/MeOH (2:1) and was dried in an oven at 62° C. overnight.

Step 5. Friedel-Crafts Acylation

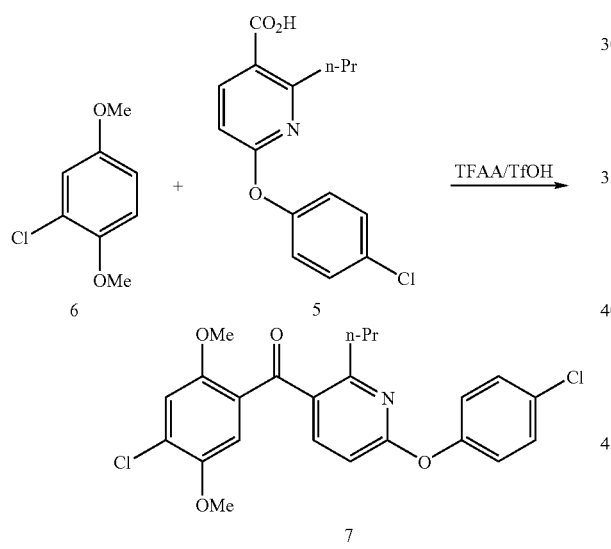

To a 100 L round bottom vessel was charged nicotinic acid 5 (7200 g, 24.68 Mol), which was then dissolved in 17 L of trifluoroacetic anhydride (TFAA). 1,4-Dimethoxy-2-chlorobenzene (6337 mL, 44.42 Mol) was added, followed by slow addition of triflic acid (4426 mL, 2 equivalents), while maintaining the temperature at <40° C. A reflux condenser was attached, and the reaction was heated to 42° C. and stirred overnight. The reaction was assayed, showing a 70% conversion by mass of 5 to 7.

An additional triflic acid charge (440 mL, 0.20 equivalents) was made, and a distillation setup was substituted for the reflux condenser. The batch was heated to 55° C., and ~9 L of TFAA was distilled into an ice cooled 22 L RBF. The batch was aged at 55° C. for 4 hours. At this point the reaction had reached completion.

The reaction was cooled to ambient temperature with an ice bath, and was then quenched into a 100 L extractor at 0° C. onto 30 L (6 molar equivalents) of 5 N KOH and 25 L (3.5 volumes) of toluene, maintaining the temperature at <50° C. for 1 hour. The 100 L flask was rinsed into the extractor with 2×2 L of toluene and 2×2 L of 5N KOH. The phases were separated at room temperature, and the organic phase was washed with 18 L of 1N HCl.

The organic solution was transferred back into the rinsed 100 L vessel and was treated with Darco G-60 (3.6 kg, 50 wt %). The mixture of solution and carbon was heated at 35° C. for 30 min. The charcoal mixture was then filtered through a pad of solka floc, rinsed with 8 L of toluene and vacuum transferred through a 5 uM poly cap, into a visually clean 100 L round bottom flask, with a mark at the 16 L level. The 100 L flask was attached to a batch concentrator and distilled down to the 16 L mark at 35° C. At this point the batch was seeded with 10 g of seed crystals of 7 obtained from an earlier batch, and heptane addition began. After 20 L of heptane had been added the slurry grew thick. The batch was heated to 55° C., and an additional 4 L of heptane was added bringing the total batch volume to the 40 L mark. The slurry was aged at 55° C. for 15 minutes with rapid stirring. At this point a constant volume distillation with the addition of heptane was begun, and the batch temperature was cooled and then was maintained between 30 and 35° C. A total of 80 L of heptane (including the original 24 L) was added to the batch. The solvent composition was checked by $^1$H NMR, and was found to contain 94 mole % heptane.

The slurry was then heated to 65° C. and allowed to slowly cool to room temperature overnight.

The slurry was filtered, and the flask was rinsed with 9 L of a mixture of 95% heptane/5% toluene. The cake was then slurry washed with 9 L of 95% heptane/5% toluene, and then 18 L heptane. The product 7 was dried on the frit under a stream of $N_2$ at ambient temperature.

Step 6. Demethylation of 7 to 8

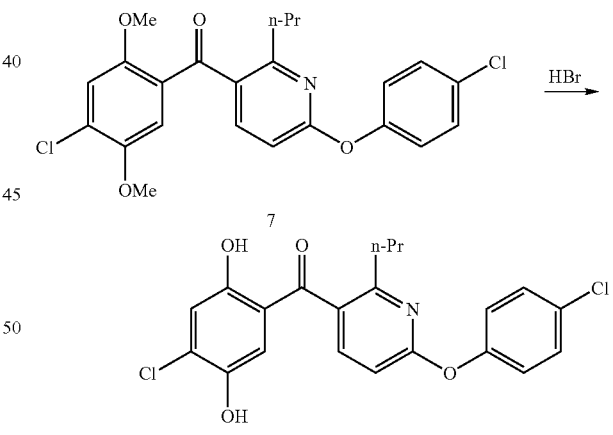

Into a visually clean 200 mL two-neck RBF was charged 11.1 g of solid 93.5 wt % dimethoxyketone 7 (25 mmol), 18.75 g sodium iodide (125 mmol), HBr (48% aqueous, 50 mL, 0.5 mol), and HOAc (50 mL, 5× vol). The slurry was heated to 100° C. (dial-in temp.) in 0.5 hours, and the internal temperature gradually stabilized at 95-95.5° C.

The slurry turned dark brown within two hours after the reaction temperature reached 90° C. Further heating for one hour gradually generated bright yellow crystals, and the precipitate became thicker with time. The reaction was stirred at 95-95.5° C. (Internal T) for 24 hours.

The batch was cooled to room temperature, filtered, and sequentially washed with 50 mL HOAc (displacement wash), 50 mL HOAc (slurry wash) and 5% MeOH in water (3×50 mL, slurry washes). The isolated product was dried at r.t. under vacuum over the weekend.

The dry powder product was then suspended in 5% MeOH in water (100 mL) for 4 hours and filtered. The filter cake was washed with 50 mL of water and dried under vacuum to give the final product as the free base.

Step 7. Oxime Formation and Isomerization

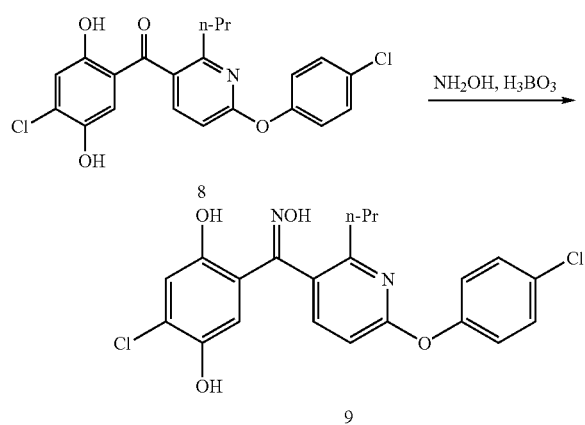

To a 100 L, 4-neck round bottom flask, with mechanical stirrer, reflux condenser, thermocouple and nitrogen/vacuum line, was charged n-propanol (24 L), dihydroquinone ketone (7.598 kg, 89% purity, 6.762 assay kg, 12.38 mol), and boric acid (808 g, 13.07 mol). Hydroxylamine (2.3 L, 37.60 mol) was then poured into the flask. The reaction was heated to reflux (90-92° C.) for 60 minutes.

The reaction was cooled to 30° C. and transferred into a 180-L extractor containing 35 L of water. 15 L of water and 50 L of MTBE were added to the extractor and the mixture was vigorously stirred and allowed to settle. The bottom aqueous layer was cut. The organic layer was washed with 50 L of 20 wt % NaCl (aq), and then with 18 L of 20 wt % NaCl (aq).

The organic layer was agitated with 3 kg of sodium sulfate and 1 kg of DARCO G-60 and filtered through a bed of Solkaflok. The cake bed was rinsed with 15 L of MTBE. The filtrate was concentrated to approximately 20 L at 35-40° C., 20-25 in. Hg. n-Propanol (60 L) was fed and distilled at 35-40° C., 28-30 in. Hg, while maintaining a constant volume of 20 L. The final batch KF was 860 ppm water.

The resulting solution was heated on a steam pot to 93-97° C. The reaction was monitored for isomerization conversion. After 6 hours, the batch was allowed to cool to ambient temperature. 200 mL of the batch was sampled for seed formation. To the stirring solution, 50 mL of water was added, and then 1 g of seed was added, and the batch was aged to form a seed bed. The remaining 250 mL of water was added to complete the crystallization.

To the batch, 5 L of water was added, followed by the seed slurry. The mixture was aged, giving a thick slurry. The remaining 25 L of water was added over 1 hour. The slurry was heated to 50° C. and cooled to ambient temperature.

The solid was isolated by filtration. The cake was washed with 2:1 water/n-propanol (8 L, 8 L, 12 L, 12 L), water (8 L), then hexanes (12 L, 8 L). The solid was dried on the filter under a nitrogen tent. The E-oxime was obtained as an orange solid.

Step 8. Benzisoxazole Formation

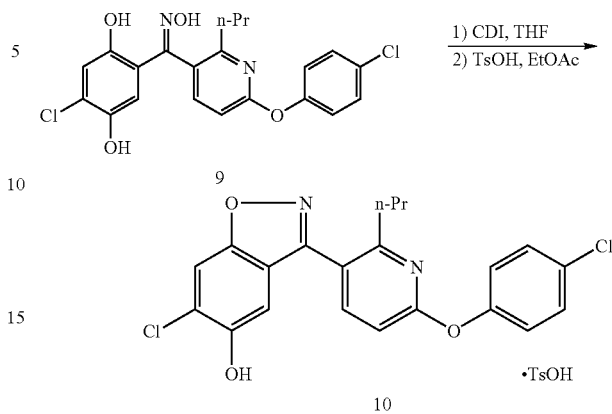

To a 100 L cylindrical vessel with cooling coils, thermocouple, and nitrogen/vacuum inlets, was charged THF (23 L) and the oxime (4.953 kg, 4.661 assay kg, 10.76 mol). The dark brown solution was cooled to −15° C. CDI (2.70 kg, 16.65 mol) was added in two portions over 10 minutes. The reaction was aged at −5-0° C. for 1 hour.

The reaction was then warmed to 25° C. MeOH (1.3 L) was added, and the solution was aged for 1 hour.

To the reaction, 35 L of MTBE, 20 L of water, and 2.5 L of 85% phosphoric acid were added with vigorous stirring. After settling, the bottom aqueous layer was cut. The organic layer was washed with water (20 L), 0.5 M Na$_2$CO$_3$ (2×20 L), 1M H$_3$PO$_4$ (20 L), then 10 wt % KH$_2$PO$_4$ (4 L).

The batch was stirred with 1 kg of DARCO G-60 for 1.5 hours. The mixture was filtered through Solkaflok and the bed was washed with 14 L of MTBE.

The filtrate was fed into a 100 L round bottom flask equipped with mechanical stirrer, thermocouple, and nitrogen inlet, and was attached to a batch concentrator. The batch was fed and distilled at 35-40° C., 16-20 in. Hg, maintaining the batch volume at 20-25 L. EtOAc (40 L) was then fed and distilled at 35-40° C., 20-23 in. Hg at a constant volume of 15-20 L.

To a 100 L cylindrical vessel with heating coils were charged EtOAc (20 L) and TsOH/H$_2$O (2.304 kg, 12.11 mol), and the mixture was heated to 35-45° C. to dissolve. The acid solution was fed into the isoxazole batch with further distilling, maintaining a constant volume of 25 L. An additional 20 L of EtOAc was distilled to azeotropically dry the mixture. A slurry began to form, and it continued to thicken on addition and concentration. The final KF was 400 ppm water. The batch was heated to 60° C. and allowed to slowly cool to ambient temperature overnight.

The solid product was isolated by filtration. The cake was washed with EtOAc (16 L), then with MeCN (24 L), and was dried on the filter under a nitrogen tent. The benzisoxazole tosylate was obtained as a pale yellow solid.

Step 9A. Lactate Tosylate Formation

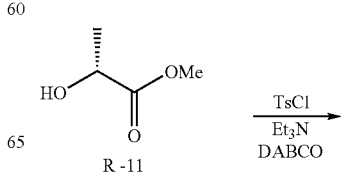

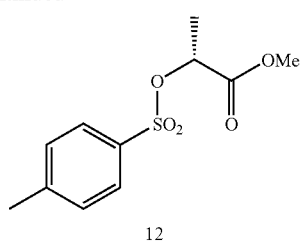

12

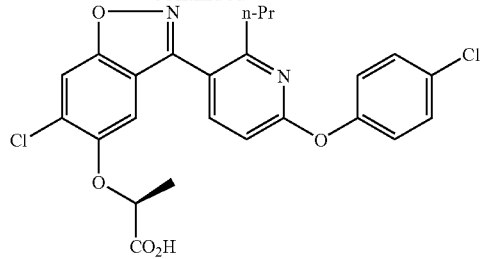

(S)-14

To a 50 L RBF was added 1.50 kg R-methyl lactate, which was then dissolved in EtOAc (7.5 L) with 3.02 kg tosyl chloride. The batch was cooled with ice to 6° C. A mild endotherm was noted on mixing.

DABCO (242 g) and triethylamine (3.01 L) were separately dissolved in the 7.5 L of EtOAc. The solution was charged to a 50 L vessel, maintaining the temperature below 25° C. The reaction was aged 2 h at room temperature. A mild to moderate delayed exotherm was seen. A white slurry formed during the addition.

To a 50 L extractor 4 L of water and 3 L of EtOAc were added with stirring. Water (3.5 L) was added to the reaction vessel, and the biphasic solution was transferred to the extractor. The vessel was then rinsed with 4.5 L EtOAc. To the stirred extraction was added 7.5 L of 2 N HCl, bringing the total extraction volume to 40 L. The extraction was aged 10 min and phase separated. The organic was washed with 7.5 L of water and then 15 L of 4% $NaHCO_3$ (aq). The organic solution was then transferred to clean plastic carboys, and dried over $Na_2SO_4$ (5 kg) in the carboys.

The batch was then filtered through a 20 uM poly cap filter into a Buchi rotary evaporator, yielding the product as an oil containing residual ethyl acetate (3 wt %) and 700 PPM water. The batch was transferred to a container and was stored in a cold room until it was used. The product had an ee of 98.2%.

Step 9. Methyl Lactate Attachment

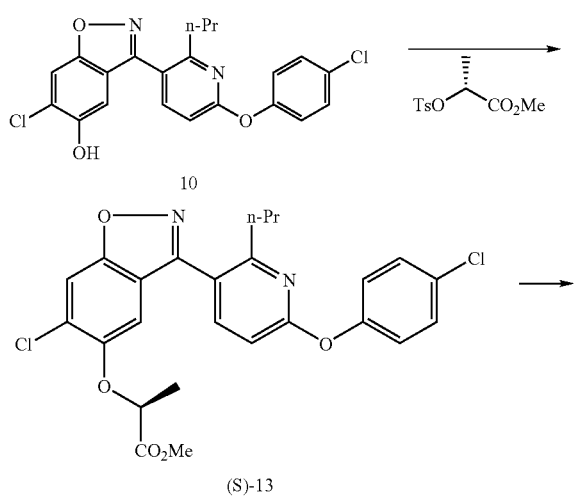

To a 100 L RBF was added benzisoxazole tosylate 10 (5.7 kg, 10 moles), then $K_2CO_3$ powder (5.7 kg, 42 moles), and then 25 L DMSO. A slight exotherm was noted. The reaction was stirred for 10 min, and the mixture was degassed and placed under $N_2$. The slurry was cooled to <30° C., and the lactate tosylate 12 (2.8 kg, 11 moles) was added. The mixture was stirred for 2-4 hrs until HPLC showed >98% conversion. To the reaction was added 20 L MTBE and 30 L cold water. The cold water was added to moderate the slight exotherm on quenching. The layers were agitated for 10 min.

The mixture was transferred to a 180 L cyclindrical vessel, and an additional 30 L MTBE and 30 L cold water were added. The layers were cut and the aqueous layer was back extracted with 25 L MTBE. The combined organic layers were washed with 18 L 2% $NaHCO_3$. The final organic layer was fed with concurrent distillation into a 100 L RBF and solvent switched to acetonitrile. The batch was kept at 25-30° C. to prevent crystallization.

The batch volume was adjusted to 45 L with acetonitile, and 36 L water was added slowly (product crystallizes after 4 L water is added). After overnight aging, the batch was filtered, and the cake was washed with 10 L 1/1 MeCN/water. Solid methyl ester S-13 on the funnel was dried with suction under nitrogen flow for 4 days.

Step 10. Hydrolysis and Final Crystallization

In a 50 L cyclindrical vessel, the methyl ester S-13 (2.3 kg) was dissolved in 12.5 L MeCN and mixed with 10 L 1N NaOH. The solution was aged for 2-3 hrs at ambient temperature. Toluene (25 L) was added, followed by conc. HCl to bring the pH to 2-3 (0.85 L). The resulting layers were separated. The organic layer was washed with 15 L brine and dried with $Na_2SO_4$ and 0.7 kg Ecorsorb C-933. The slurry was filtered and the cake was washed with 10 L toluene. In a 100 L RBF, the filtrate was batch concentrated to 15 L.

The batch volume was then adjusted to 18 L (8 L toluene/ kg product). The batch was heated to 50° C., and 56 L of methylcyclohexane was added at 50° C. The batch was seeded with crystals from earlier batches after 18 L of methylcyclohexane was added. The batch was cooled slowly to ambient temperature (about 10 min per degree) to yield crystalline product S-14. The batch became thick at around 39° C. The batch was cooled further to ambient temperature over 4-8 hrs. It was aged a total of 16 hrs.

The batch was filtered, and the cake was washed with 10 L of 4:1 methylcyclohexane/toluene, then 2×10 L of methylcyclohexane. It was dried on the filter pot under vacuum and nitrogen flow overnight, and was then transferred to a vacuum oven and dried with nitrogen flow overnight.

Crystalline Anhydrous Tosylate Salt

The crystalline anhydrous tosylate salt of compound I was prepared by the following method from the methyl ester of compound I. MeCN (110 kg) was charged to a reactor. The methyl ester of Compound I (e.g. from step 9 of Example 1; 29.9 kg; 59.6 moles) was charged to the reactor, followed by a MeOH flush of the charge valve. 135 kg of 1.0N NaOH (~131 moles) was added, followed by a water flush at 15-25° C. The solution was aged for 2-3 hours at 15-25° C. and then assayed for completion of the reaction.

Concentrated 5N HCl (26.7 kg) was added using a pump to adjust the pH to 2-3. The solution was extracted with 295 kg ethyl acetate. The organic layer was separated from the aqueous layer and washed with 215 kg of 18% brine solution.

The batch was filtered via a 0.6 micron filter and concentrated to 200-220 L at <40° C. and reduced pressure. The solvent was switched at constant volume to EtOAc at <40° C. and reduced pressure (~125 to 252 mmHg). The water concentration by Karl Fischer titration was 72.3 µg/ml, the product concentration was 135.5 g/L, and the acetonitrile content was 0.36 v/v %. The batch was collected in drums.

A solution of p-toluenesulfonic acid monohydrate (12 kgs; 62 moles) in ethyl acetate (135 kgs) was prepared and was also collected in drums.

A charge of 60 kg EtOAc was added to the crystallizer through a 0.6 micron filter. A seed slurry (about 12.9 kg containing about 1 kg of media-milled tosylate seed in about 10 L ethyl acetate) was added to the reactor followed by about 10 kg of a pre-filtered EtOAc wash. The seed slurry was recycled from the bottom of the reactor through the outlet and back in through the inlet. Then, the batch of Compound I in EtOAc and the solution of p-toluenesulfonic acid (p-TSA) in EtOAc solution were charged simultaneously into the reactor over a period of about 8 hours. The charge rates for the concentrated batch and p-TSA/EtOAc solution were 0.3 kg/L and 0.4 kg/L respectively. The temperature was maintained at 15 to 25° C. After crystallization the batch was aged at 15 to 25° C. for 2 hours.

Seeds for the crystallization step above are saved from earlier batches of Compound I tosylate. The same crystalline product can also be obtained without seed crystals if none are available.

The batch was filtered and the cake was washed with a total of ~240 kg ethyl acetate. The batch was dried under vacuum at 40° C., yielding about 35.8 kg of the desired tosylate salt, for a yield of 90.5% for the salt preparation. The dried batch was delumped prior to further use.

Dosage Form

The anhydrous crystalline tosylate salt of Compound I is formulated as either dry filled capsules or compressed tablets in doses that generally will range from 1 mg to 25 mg of API as the free acid (non-salt). Typically, the doses will be in the range of 2-10 mg. A typical capsule or tablet formulation contains the anhydrous crystalline tosylate salt, microcrystalline cellulose (Avicel), lactose monohydrate, croscarmellose sodium, sodium lauryl sulfate, and magnesium stearate. The capsule formulations are transferred to a capsule made of gelatin, titanium dioxide, and ferric oxide. Tablet formulations are coated with a functional film coat containing lactose, hypromellose, triacetin, titanium dioxide, and ferric oxide. The capsule shell and tablet film coating are opaque to protect the active compound from exposure to light.

The formulations are manufactured by first blending the excipients, then compressing the mixture into ribbons by roller compaction, and then milling the ribbons into granules. The granules are then lubricated and either filled into capsules or compressed into tablets. If tablets are selected, a film coat is applied to the compressed tablets.

Exemplary fill formulations that provide a 5 mg or 10 mg dose of Compound I in a standard gelatin capsule are shown below. The components are combined, compressed and milled as described above, and then the amount of milled formulation that contains the 5 mg or 10 mg dose of Compound I is transferred to each capsule. The salt factor for the anhydrous crystalline tosylate salt of Compound I is 1.353.

| Components | 5 mg Dose | 10 mg Dose |
| --- | --- | --- |
| Compound I (weight of API) | 6.765 mg | 13.53 mg |
| Microcrystalline cellulose (Avicel) | 43.62 mg | 40.235 mg |
| Lactose monohydrate (Diluent) | 43.62 mg | 40.235 mg |
| Croscarmellose sodium (Disintegrant) | 3 mg | 3 mg |
| Sodium lauryl sulfate (surfactant) | 2 mg | 2 mg |
| Magnesium stearate (lubricant) | 1 mg | 1 mg |

Characterization of the Crystalline Anhydrous Tosylate Salt

X-ray powder diffraction studies are widely used to characterize molecular structures, crystallinity, and polymorphism. The X-ray powder diffraction patterns of the crystalline anhydrous tosylate salt were generated on a Philips Analytical X'Pert PRO X-ray Diffraction System with a PW3040160 console. A PW3373/00 ceramic Cu LEF X-ray tube K-Alpha radiation was used as the source.

FIG. 1 shows the X-ray diffraction pattern for the crystalline anhydrous tosylate salt, Form I. The crystalline anhydrous tosylate salt exhibited characteristic reflections corresponding to d-spacings of 13.52, 6.92, and 6.24 angstroms. The crystalline anhydrous tosylate salt was further characterized by reflections corresponding to d-spacings of 9.93, 5.73 and 4.59 angstroms. The crystalline anhydrous tosylate salt was even further characterized by reflections corresponding to d-spacings of 8.43, 5.54 and 3.53 angstroms.

In addition to the X-ray powder diffraction patterns described above, the crystalline anhydrous tosylate salt was further characterized by solid-state carbon-13 nuclear magnetic resonance (NMR) spectra. The solid-state carbon-13 NMR spectra were obtained on a Bruker DSX 500WB NMR system using a Bruker 4 mm H/X/Y CPMAS probe. The carbon-3 NMR spectra utilized proton/carbon-13 cross-polarization magic-angle spinning with variable-amplitude cross polarization, total sideband suppression, and SPINAL decoupling at 100 kHz. The samples were spun at 10.0 kHz, and a total of 2048 scans were collected with a recycle delay of 5 seconds. A line broadening of 10 Hz was applied to the spectra before FT was performed. Chemical shifts are reported on the TMS scale using the carbonyl carbon of glycine (176.03 p.p.m.) as a secondary reference.

Figure 2:
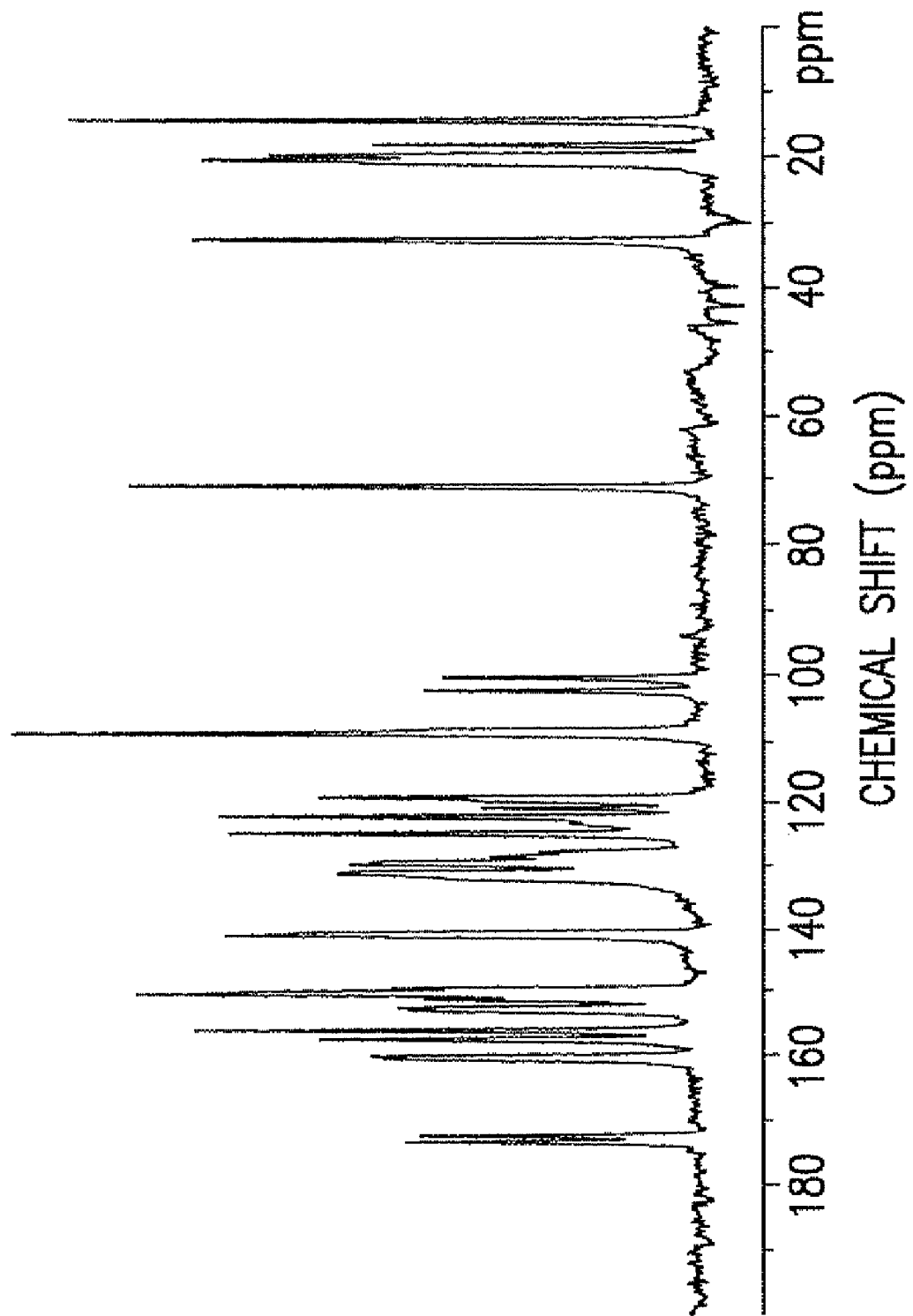
FIG. 2 is a carbon-13 cross-polarization magic-angle spinning (CPMAS) nuclear magnetic resonance (NMR) spectrum of the crystalline anhydrous tosylate salt.

FIG. 2 shows the solid-state carbon-13 CPMAS NMR spectrum for the crystalline anhydrous tosylate salt. The crystalline anhydrous tosylate salt exhibits characteristic signals with chemical shift values of 109.5, 14.5, 71.2, and 150.4 p.p.m. Further characteristic of the crystalline anhydrous tosylate salt are the signals with chemical shift values of 32.9, 156.1, 20.8, and 122.4 p.p.m. The crystalline anhydrous tosylate salt is even further characterized by signals with chemical shift values of 141.2, 18.2, and 173.2 p.p.m.

DSC data were acquired using TA Instruments DSC 2910 or equivalent instrumentation. Between 2 and 10 mg sample was weighed into an open pan and lid was placed lightly to cover the sample. This covered pan was then placed at the sample position in the calorimeter cell. An empty pan with lid was placed at the reference position. The calorimeter cell was closed and a flow of nitrogen was passed through the cell. The heating program was set to heat the sample at a heating rate of 10° C./min to a temperature of approximately 250° C. The heating program was then started. When the run was completed, the data were analyzed using the DSC analysis program contained in the system software. The melting endotherm was integrated between baseline temperature points that are above and below the temperature range over which the endotherm was observed. The data reported are the onset temperature, peak temperature and enthalpy.

Figure 3:
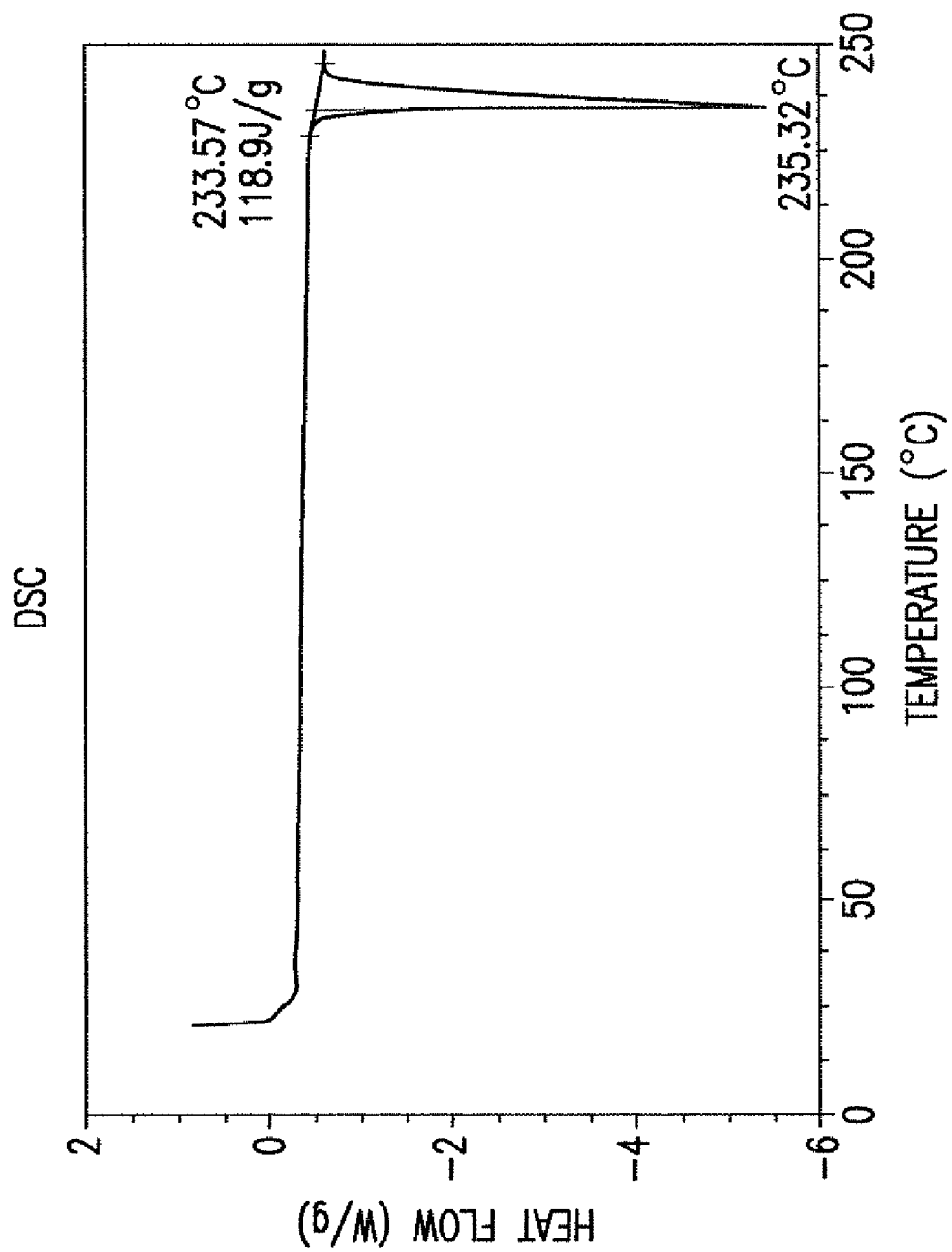
FIG. 3 is a typical DSC curve of the crystalline anhydrous tosylate salt.

FIG. 3 shows the differential calorimetry scan for the crystalline anhydrous tosylate salt. The crystalline anhydrous tosylate salt exhibited a single endotherm due to melting with an onset temperature of 233.6° C., a peak temperature of 235.3° C., and an enthalpy change of 118.9 J/g.

What is claimed is:

1. The compound (2S)-2-({6-chloro-3-[6-(4-chlorophenoxy)-2-propylpyridin-3-yl]-1,2-benzisoxazol-5-yl}oxy) propanoic acid having formula I:

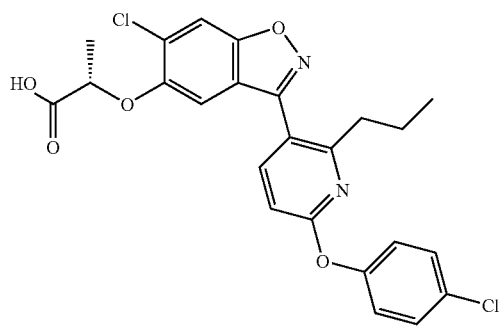

I characterized as being a crystalline anhydrous toluenesulfonic acid salt.

2. The crystalline anhydrous toluenesulfonic acid salt of claim 1 having one or more spectral characteristics selected from the X-ray powder diffraction pattern, a solid-state carbon-13 CPMAS nuclear magnetic resonance spectrum, and a differential scanning calorimetric (DSC) curve.

3. The compound of claim 1 characterized as being a crystalline anhydrous toluenesulfonic acid salt having X-ray powder diffraction peaks corresponding to d-spacings of 13.52, 6.92, and 6.24 angstroms.

4. The compound of claim 1 characterized as being a crystalline anhydrous toluenesulfonic acid salt having X-ray powder diffraction peaks corresponding to d-spacings of 9.93, 5.73 and 4.59 angstroms.

5. The compound of claim 1 characterized as being a crystalline anhydrous toluenesulfonic acid salt having X-ray powder diffraction peaks corresponding to d-spacings of 8.43, 5.54 and 3.53 angstroms.

6. The compound of claim 1 characterized as being a crystalline anhydrous toluenesulfonic acid salt having peaks in the solid-state carbon-13 CPMAS nuclear magnetic resonance spectrum having chemical shift values of 109.5, 14.5, 71.2, and 150.4 p.p.m.

7. The compound of claim 1 characterized as being a crystalline anhydrous toluenesulfonic acid salt having peaks in the solid-state carbon-13 CPMAS nuclear magnetic resonance spectrum having chemical shift values of 32.9, 156.1, 20.8, and 122.4 p.p.m.

8. The compound of claim 1 characterized as being a crystalline anhydrous toluenesulfonic acid salt having peaks in the solid-state carbon-13 CPMAS nuclear magnetic resonance spectrum having chemical shift values of 141.2, 18.2, and 173.2 p.p.m.

9. The compound of claim 1 characterized as being a crystalline anhydrous toluenesulfonic acid salt having an endotherm in the differential calorimetry scan with an onset temperature of 233.6° C. and a peak temperature of 235.3° C.

10. A pharmaceutical composition comprising a therapeutically effective amount of the crystalline anhydrous toluenesulfonic acid salt of claim 1 in association with one or more pharmaceutically acceptable carriers or excipients.

11. The toluenesulfonic acid salt of (2S)-2-({6-chloro-3-[6-(4-chlorophenoxy)-2-propylpyridin-3-yl]-1,2-benzisoxazol-5-yl}oxy)propanoic acid having formula Ia:

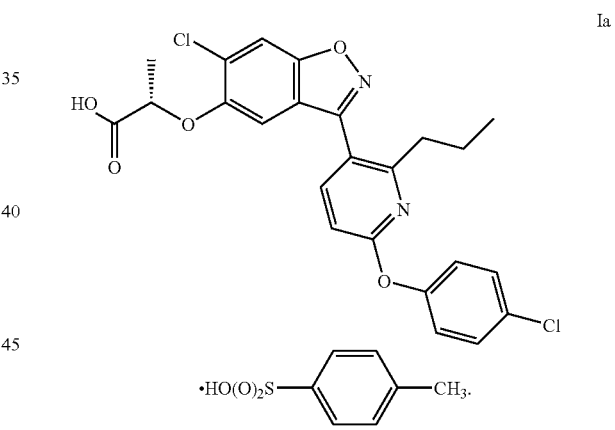

Ia

* * * * *